United States Patent [19]
Clawson et al.

[11] Patent Number: 6,078,894
[45] Date of Patent: Jun. 20, 2000

[54] METHOD AND SYSTEM FOR EVALUATING THE PERFORMANCE OF EMERGENCY MEDICAL DISPATCHERS

[76] Inventors: Jeffrey J. Clawson, 4649 Farm Meadow La., Salt Lake City; Richard Saalsaa, 4449 Heatherview Ct., West Valley City, both of Utah

[21] Appl. No.: 08/832,612

[22] Filed: Mar. 28, 1997

[51] Int. Cl.[7] ................................................. G06F 17/60
[52] U.S. Cl. .............................. 705/11; 705/2; 705/7; 379/45; 364/468.15
[58] Field of Search ..................... 705/2, 11, 7; 436/510; 379/45; 364/468.15

[56] References Cited

U.S. PATENT DOCUMENTS

| | | | |
|---|---|---|---|
| 4,130,881 | 12/1978 | Haessler et al. | 705/3 |
| 4,237,344 | 12/1980 | Moore | 379/38 |
| 4,489,387 | 12/1984 | Lamb et al. | 395/200.67 |
| 4,839,822 | 6/1989 | Dormond et al. | 706/45 |
| 4,858,121 | 8/1989 | Barber et al. | 705/2 |
| 4,945,476 | 7/1990 | Bodick et al. | 600/301 |
| 5,063,522 | 11/1991 | Winters | 706/10 |
| 5,065,315 | 11/1991 | Garcia | 705/2 |
| 5,072,383 | 12/1991 | Brimm et al. | 705/2 |
| 5,253,164 | 10/1993 | Holloway et al. | 705/2 |
| 5,255,187 | 10/1993 | Sorensen | 600/300 |
| 5,339,351 | 8/1994 | Hoskinson et al. | 379/45 |
| 5,471,382 | 11/1995 | Tallman et al. | 600/300 |
| 5,516,702 | 5/1996 | Senyei et al. | 436/510 |
| 5,596,994 | 1/1997 | Bro | 600/545 |
| 5,805,670 | 9/1998 | Pons et al. | 379/45 |

OTHER PUBLICATIONS

Lynda Radosevich, Network holds sway on life, death, computerworld v27n21, pp. 57, May 1993.

Geac Completes Software Install, Wireless week, pp. 26, Nov. 1996.

Roger Harris, Updated 911 phone system top concern to Residents, Business First–Louisville, v9n19, Dec. 1992.

Dictaphone Introduces Windows–based Computer–Aided Dispatch (CAD) system *in commercial use in 1995, Apr. 1996.

Holroyd, Brian, Medical Control; Quality Assurance in prehospital care,Jama, the journal of the American Medical Association, Aug. 1986.

*Primary Examiner*—Stephen R. Tkacs
*Assistant Examiner*—Raquel Alvarez
*Attorney, Agent, or Firm*—Lloyd W. Sadler

[57] ABSTRACT

A method and system for evaluating the performance of emergency medical dispatchers in adhering to a provided systematic procedure or protocol for handling emergency medical calls is described. This invention provides a systematic, objective, approach to grading the dispatcher's response and thereby providing for continuous quality assurance and improvement of the dispatcher's skills. In its preferred embodiment, this invention is performed in computer software which enhanced the evaluation process by working in association with a computerized emergency medical dispatch protocol to accumulate data and efficiently grade the performance of the dispatcher.

1 Claim, 7 Drawing Sheets

METHOD AND SYSTEM FOR EVALUATING THE PERFORMANCE OF EMERGENCY MEDICAL DISPATCHERS

BACKGROUND OF THE INVENTION

1. Field of the Invention.

This invention relates to methods and systems for evaluating and providing quality assurance to emergency medical dispatchers who are processing emergency medical calls and who have been trained to process such calls using the Advanced Medical Priority Dispatch System. Specifically, this invention relates to the process of providing a consistent measurable method of evaluating the compliance of emergency medical dispatchers with the protocols and procedures incorporated in the Advanced Medical Priority Dispatch System. Providing adequate emergency medical care presents several critical challenges to medical care providers. Once of the most important of these challenges is assuring continuous improvement in the quality of work of medical dispatchers. To achieve continuous improvement in quality, a measurable standard must be made and a method must be provided to measure the performance of individual dispatchers against this standard. This invention addresses these challenges by providing a system and process for scoring the dispatcher's compliance with established medical procedures.

The Advanced Medical Priority Dispatch System is a systematic process for guiding emergency medical dispatchers through established medically sound protocols for responding to emergency medical calls, gathering the critical information from the caller, identifying the chief complaint and categorizing its criticality, dispatching emergency medical responders and providing the responders with all helpful information for treating the complaint, and giving continued emergency medical instructions and guidance to the caller. Studies conducted by Medical Priority Consultants, and the Los Angeles Fire Department, and the Clark County Regional Communication Center, Washington, have shown that the greater the compliance with the Advanced Medical Priority Dispatch System protocols and procedures, the greater the demonstrated ability of the emergency medical dispatcher to determine the closest approximate chief complaint and the resulting determinant of appropriate response. Therefore, when the dispatcher follows with a high degree of compliance at the time of the dispatch the Advanced Medical Priority Dispatch System protocols, the patient at the scene of the emergency receives better response and better treatment, while emergency medical responders are given better information as to both the type of emergency and the appropriate level of urgency.

This invention is designed to provide a method and system for providing quality assurance of the emergency dispatchers' skills in following the provided protocols.

While this invention is designed to function in association with the Advanced Medical Priority Dispatch System, many of the methods and procedures are applicable to being applied in a more general quality assurance process for individuals whose work requires a high degree of compliance with established procedures and/or protocol. The applicant intends that this invention be interpreted to include such application of the practice of this invention.

2. Description of Related Art.

It is desirable to provide a systematic and standardized method for evaluating the compliance with established emergency medical procedures and protocols by emergency medical dispatchers in their responses to emergency medical requests. Although methods for testing and evaluation of performance are well known in the related art, the inventors know of no method or process which addresses the important quality assurance and grading requirements of compliance with medical procedure and protocols by emergency medical dispatchers. The applicant is unaware of any issued or pending U.S. or foreign patents in this area.

SUMMARY OF THE INVENTION

It is desirable to provide a system for the evaluation and quality assurance of compliance with procedures and protocols for emergency medical dispatchers. Furthermore, it is desirable to provide a system that consistently and measurably improves the accuracy and appropriateness of patient interrogation and resulting response generation. Such a system can improve the skills of dispatchers, formalizing their roll as part of the professional chain of patient care. It is also desirable to have a method grading the performance of emergence medical dispatchers that minimizes the time, cost and skill required for evaluation of the dispatchers, while improving the consistency and objectivity of such grading and evaluation. It is desirable to provide a method for evaluation of medical dispatchers which includes weighted scoring based on the equality and relationship between case entry, key questions, caller instructions, accuracy of the identification of the initial chief complaint, and the accuracy of the dispatch coding.

Accordingly, it is the primary object of this invention to provide a method for evaluating the performance of emergency medical dispatchers in their compliance with the procedures and protocols for responding to emergency medical calls.

Another object of this invention is to provide system and method for scoring the performance of emergency medical dispatchers, thereby providing an objective quality assurance method for continuous improvement of emergency medical dispatchers skills.

A further object of this invention is to improve the quality and efficiency of emergency medical dispatchers and to do so in a manner which minimizes the cost and effort of evaluation while simultaneously improving the usefulness of the scoring information produced.

These and other objects of this invention, which will be clear to those of ordinary skill in the art upon review of this patent specification and claims, are achieved by an invention which provides a method and system for reviewing, scoring and evaluating the emergency medical dispatcher responses, questions and instructions to calls received by the dispatcher.

The method and system of this invention is currently envisioned in a computerized software embodiment, although the essence of the invention can be practiced, if somewhat less efficiently, without the aid of computers.

DETAILED DESCRIPTION OF THE INVENTION

This invention provides a method and system for evaluating, scoring and assuring the quality of emergency medical dispatch response interrogation, communications and the providing of information to callers and responders. When the invention is properly employed the compliance and quality of emergency dispatcher service is improved, thereby providing better emergency medical care to patients through the callers.

Figure 1:
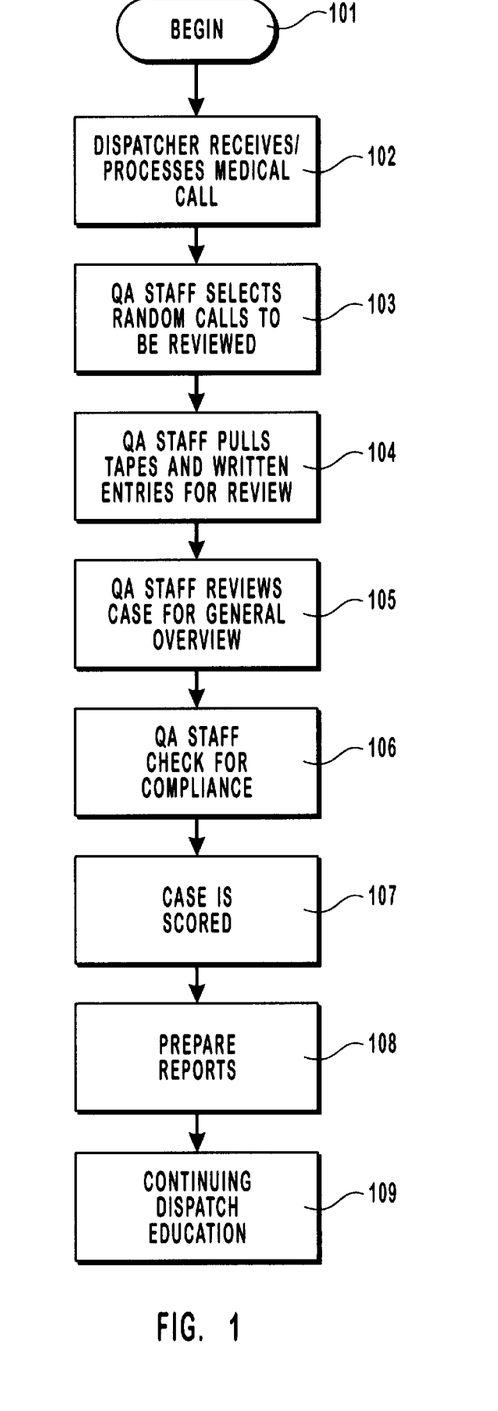
FIG. 1 depicts the workflow process of the evaluation system that is the invention.

FIG. 1 shows the workflow process of the evaluation system that incorporates the invention. The process begins 101 with the training of the emergency medical dispatchers in the Advanced Medical Priority Dispatch System (AMPDS) including the procedures and protocols. Next, the dispatcher receives and processes 102 an emergency medical call, using the AMPDS in either the manual or the computerized form. At some periodic basis random calls are selected 103 for review. Tapes and written entries are pulled for review 104. The entire case is reviewed to gain an overview of the call and its context 105. Then, the call is reviewed in detail to check 106 for compliance with each of the five sections of AMPDS. The case is then scored 107. Reports are prepared 108 showing the compliance for a given time period by individual, group or as a emergency medical dispatch center. The prepared reports are scanned, looking for problems with compliance to a given chief complaint, or with certain functions of the AMPDS in general. Then the evaluation is applied to improve performance through continued dispatch education 109 or remedial training to correct problems in AMPDS delivery, and to increase compliance.

The scoring method of step 107 is accomplished in the following manner. Scoring is based on each of the five areas of the AMPDS dispatch protocol: Case Entry; Key Question; PDI or PAI; Chief Complaint; and Final Coding. Case Entry is scored with the following weighting. Age asked (yes or obvious) is weighted 33%, Conscious asked (yes or obvious) is weighted 33% and Breathing asked (yes or obvious) is weighted 33%. Additionally, certain penalties are imposed for errors in emergency call processing. These penalties include: 10% if questions are not asked in order; 20% if conscious and breathing are asked as one question, 5% if the callers address is not verified; 5% if the callback is not verified and 5% based on the beginning emotional content/cooperation score and use of calming techniques.

Key Questions are scored as follows. Each question is given two points. One point is given for asking the question and one point is for asking the question correctly. The total number of points are added and divided by the total number of questions possible times 2 to find the percentage score. For example, if five questions are possible then ten points are possible. If three questions are asked correctly then 3×2=6, one question is asked but not correctly=1 point, and one question not asked at all=0 points. Total points given 6+1+0=7 out of 10 possible or 70%.

The PDI/PAI score is weighted as follows. PDIs (Post-Dispatch Instructions) and PAIs (Pre-Arrival Instructions) are scored in a mutual exclusive manner. That is, only one or the other are scored. If PDIs are scored PDA's are ignored while if PDAs are scored PDIs are ignored. If the PAI is appropriate but is not given, then a score of 0% is awarded. If the PAI is given, but with minor and/or unwarranted deviation, a score of 90% is given. If the PAI is given, but with a moderate deviation or omission, then a score of 75% is given. If the PAI is given, but ad-libbed as to 50% or more of the instructions, then a score of 50% is given. If it is not possible to give the PAI then a score of 100% is given. If it is possible to give a PDI and a PDI is not given then the score is 0%. If the PDI is given with minor and/or unwarranted deviation then a score of 90% is given. If the PDI is given but with moderate deviation or omission then a score of 75% is given. If the PDI is given but is ad-libbed as to 50% or more of the instructions then a score of 50% is given. If PAIs are not appropriate and PDIs are not possible to give then a score of 100% is given.

If the Chief Complaint entry is not correct then the score for chief complaint is 0%.

The final coding score is made by the following process. If the chief complaint code is incorrect then the score is deducted 40%, if the level is incorrect the score is deducted by 40% and if the sub-determinant is incorrect then the score is deducted by 20%.

The Total Score is composed of each of the five parts, each of equal weight (20%). For example if a dispatcher scored 100% on Case Entry
80% on Key Questions
100% on Pre-Arrival Instructions
100% on Chief Complaint and
100% on Final Coding, then the dispatcher's Total Score would be 96%

Figure 2:
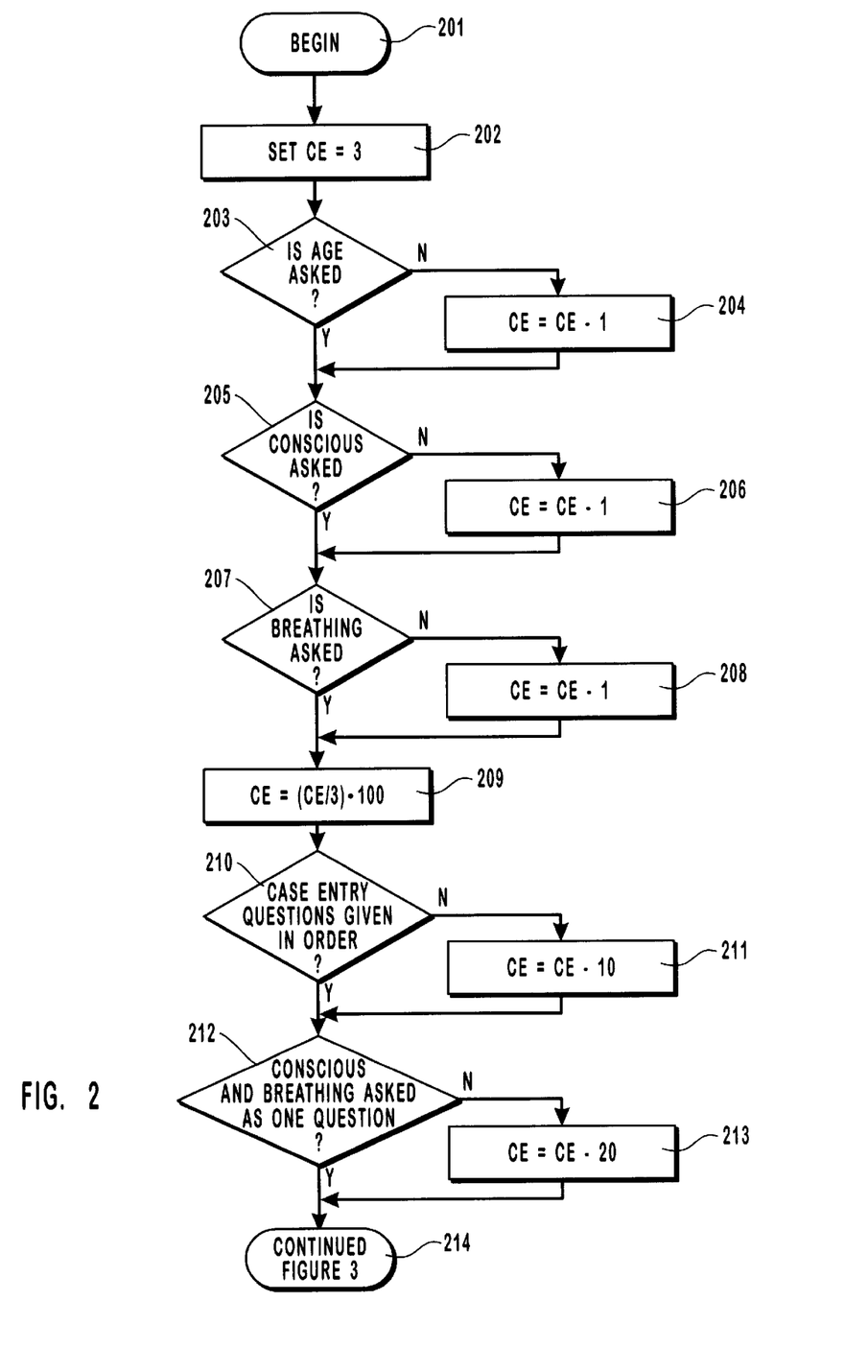
FIGS. 2 through 4 depicts the detailed flow chart of the top level software of the preferred embodiment of the invention.
Figure 3:
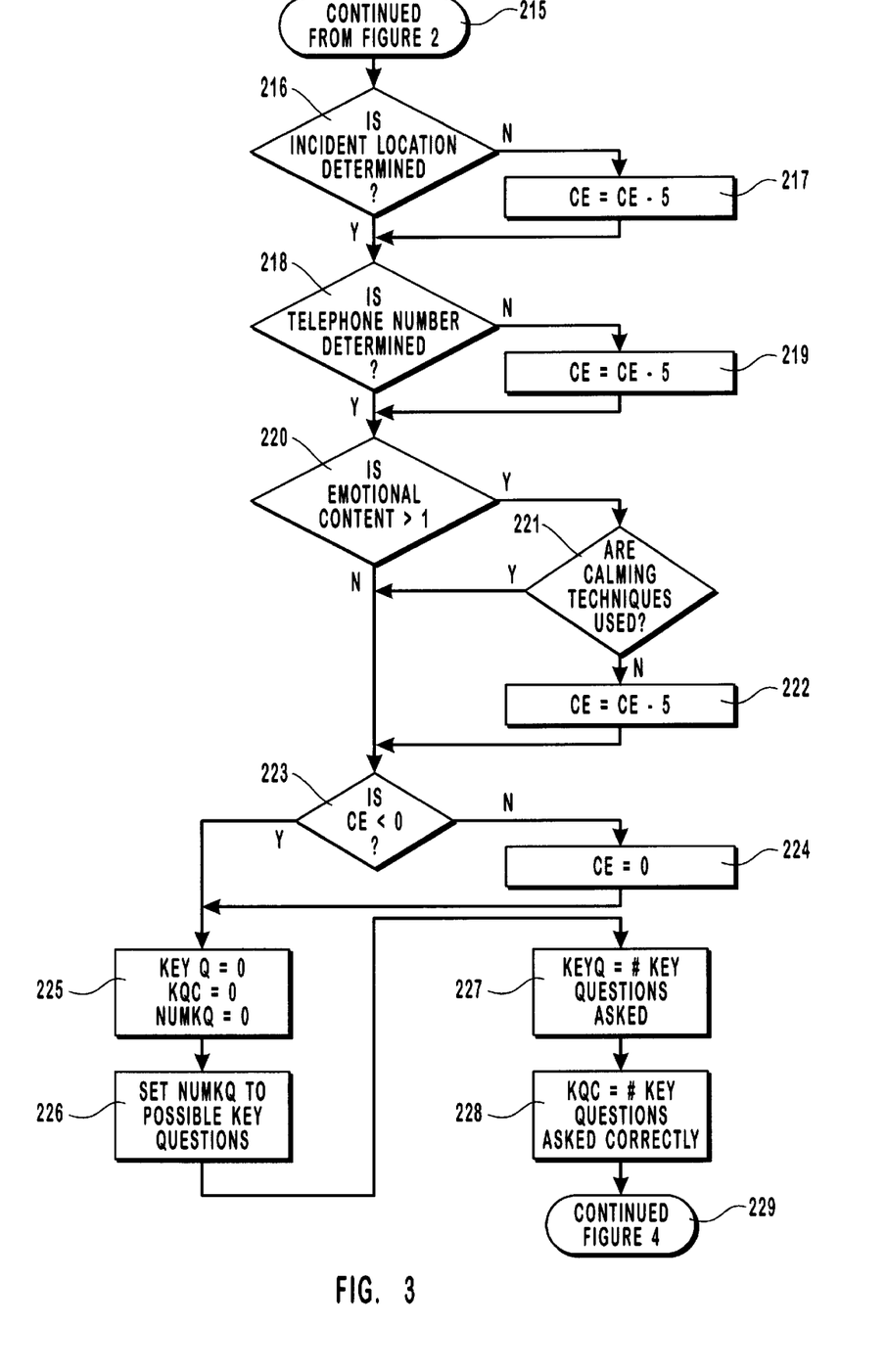
Figure 4:
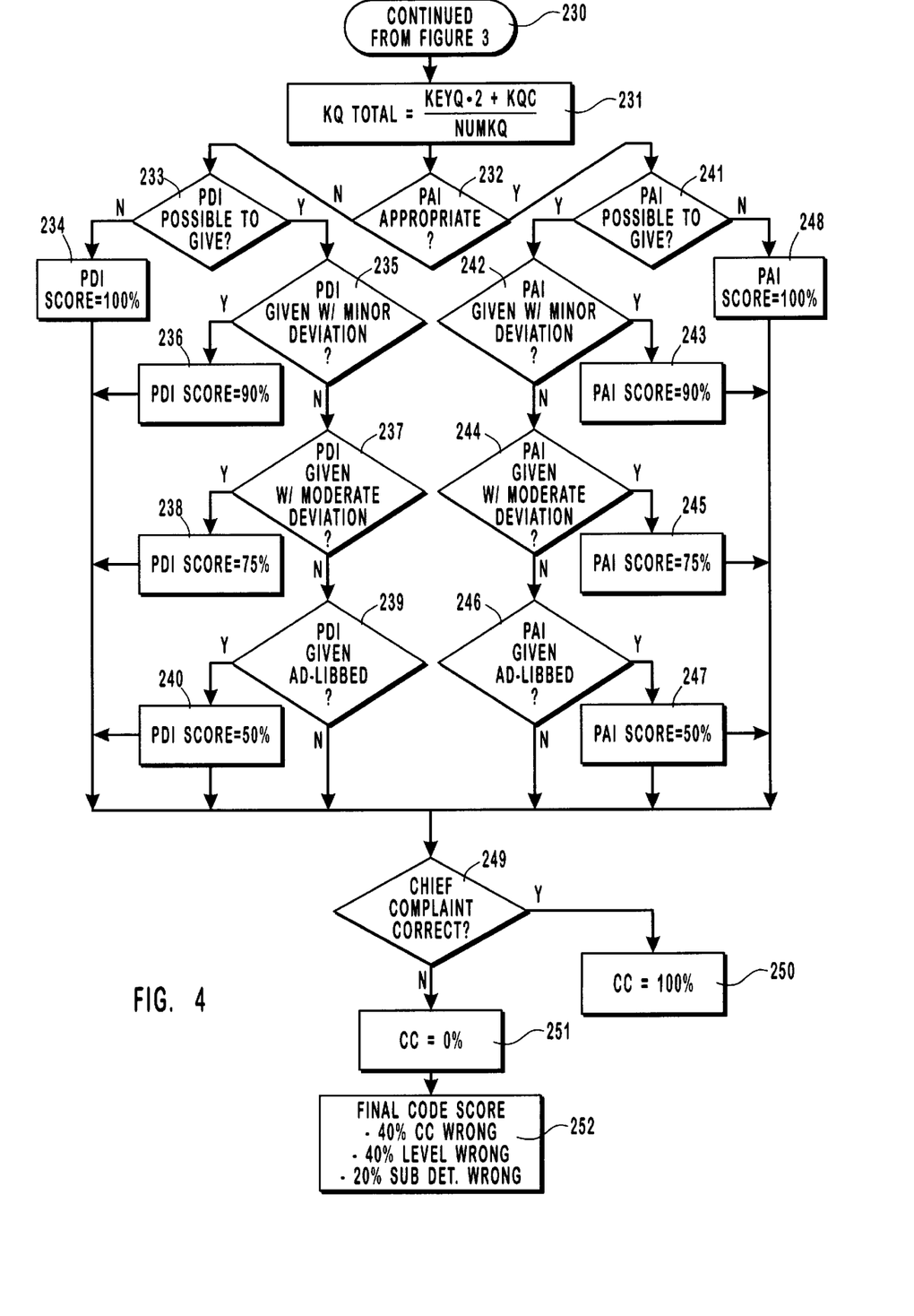

FIGS. 2 through 4 are the detailed flow chart of the preferred software embodiment of the invention, further described as follows. The process of evaluating the performance of the emergency medical dispatcher begins 201 and the case entry (CE) variable is initialized 202 to a value of 3. A test 203 is made to determine whether the dispatcher inquired of the age of the patient. If the dispatcher neglected to ask the age question then the value of CE is decremented 204. If the dispatcher inquired as to the patient's age or after the value of CE is decremented 204, a test 205 is made to determine whether the dispatcher inquired as to whether the patient is conscious. If the dispatcher neglected to ask the conscious question then the value of CE is decremented 206. If the dispatcher inquires whether the patient is conscious, or after CE is decremented 206, a test 207 is made to determine if the dispatcher inquired as to whether the patient is breathing. If the dispatcher neglected to ask the breathing question then the value of CE is decremented 208. If the dispatcher inquired as to whether the patient is breathing or after the value of CE is decremented 208, then the value of CE is set 209 to its previous value divided by 3 and multiplied by 100. Next, a test 210 is made to determine whether the dispatcher asked the case entry questions (age, consciousness, and breathing) in order. If the dispatcher failed to ask the case entry questions in order the value of CE is decreased 211 by ten. Next, a test 212 is made to determine if the dispatcher asked the consciousness and breathing inquiries as one question. If the dispatcher did ask both as one question, then the value of CE is decreased 213 by twenty. The process continues 214 on FIG. 3. FIG. 3 continues 215 the preferred process steps of this invention. A test 216 is made to determine if the dispatcher determined the location of the incident. If the dispatcher failed to locate the incident, the value of CE is decreased 217 by five. Next, A test 218 is made to determine if the dispatcher determined the caller's telephone number. If the dispatcher failed to determine the caller's telephone number, then the value of CE is decreased 219 by five. Next, a test 220 is made to determine the emotional content of the caller, if so, a follow-up test 221 is made to determine if the dispatcher used calming techniques. If the emotional content is high and the dispatcher did not use calming techniques, then the value of CE is reduced 222 by five. Next, a test 223 is made to determine if the value of CE is less than zero. If CE is less than zero, it is reset 224 to zero. Next, the variables KEYQ, KQC and NUMKQ are set 225 to zero. NUMKQ is set 226 to the number of possible key questions. KEYQ is set 227 to the number of key questions asked. KQC is set 228 to the number of key questions asked correctly. This process continues 229 on FIG. 4. FIG. 4 continues 230 this preferred process of this invention. KQTOTAL is set 231 equal to (KEYQ*2+ KQC)/NUMKQ. Next, a test 232 is made to determine if a pre-arrival instruction (PAI) is appropriate for the situation. If it is, then a test 241 is made to determine if it possible to give the PAI. If it is not, then the PAI score is set 248 to 100% and the process goes to step 249. If it is possible to give the PAI, a test 242 is made to determine if the PAI was given with minor deviation. If yes, then the PAI score is set 243 to 90%. If the PAI was not given with minor deviation, then a test 244 is made to determine if the PAI was given with moderate deviation. If yes, then the PAI score is set 245 to 75%. If the PAI was not given with moderate deviation, then a test 246 is made to determine if the PAI was give in an adlibbed fashion. If the PAI was given in an adlibbed fashion, then the PAI score is set 247 to 50%. If it was not possible to give the PAI, from test step 241, then the PAI score is set 248 to 100%.

If the test 232 resulted in an indication that PAI is not appropriate, then a test 233 is made to determine if it is possible to give the pre-dispatch instructions (PDI). If it is not possible to give the PDI, then the PDI score is set 234 to 100%. If it is possible to give the PDI, then a test 235 is made to determine whether the PDI was give with minor deviations. If the PDI was given with only minor deviations the PDI score is set 236 to 90%. If the PDI was given without only minor deviations then a test 237 is made to determine if the PDI was given with moderate deviations. If the PDI was given with moderate deviations then the PDI score is set 238 to 75%. If the PDI was not given with only moderate deviations then a test 239 is made to determine if the PDI was adlibbed. If the PDI was adlibbed then the PDI score is set 240 to 50%.

Next, a test 249 is made to determine if the dispatcher correctly determined the chief complaint. If the chief complaint is correct then CC is set 250 to 100%. If the chief complaint is not correct, CC is set 251 to 0%. Lastly, the final code score is set 252. Preferably, the final code score is reduced by 40% if the chief compliant is wrong, 40% if the determinant level is wrong and 20% if the subdeterminant is wrong.

Figure 5:
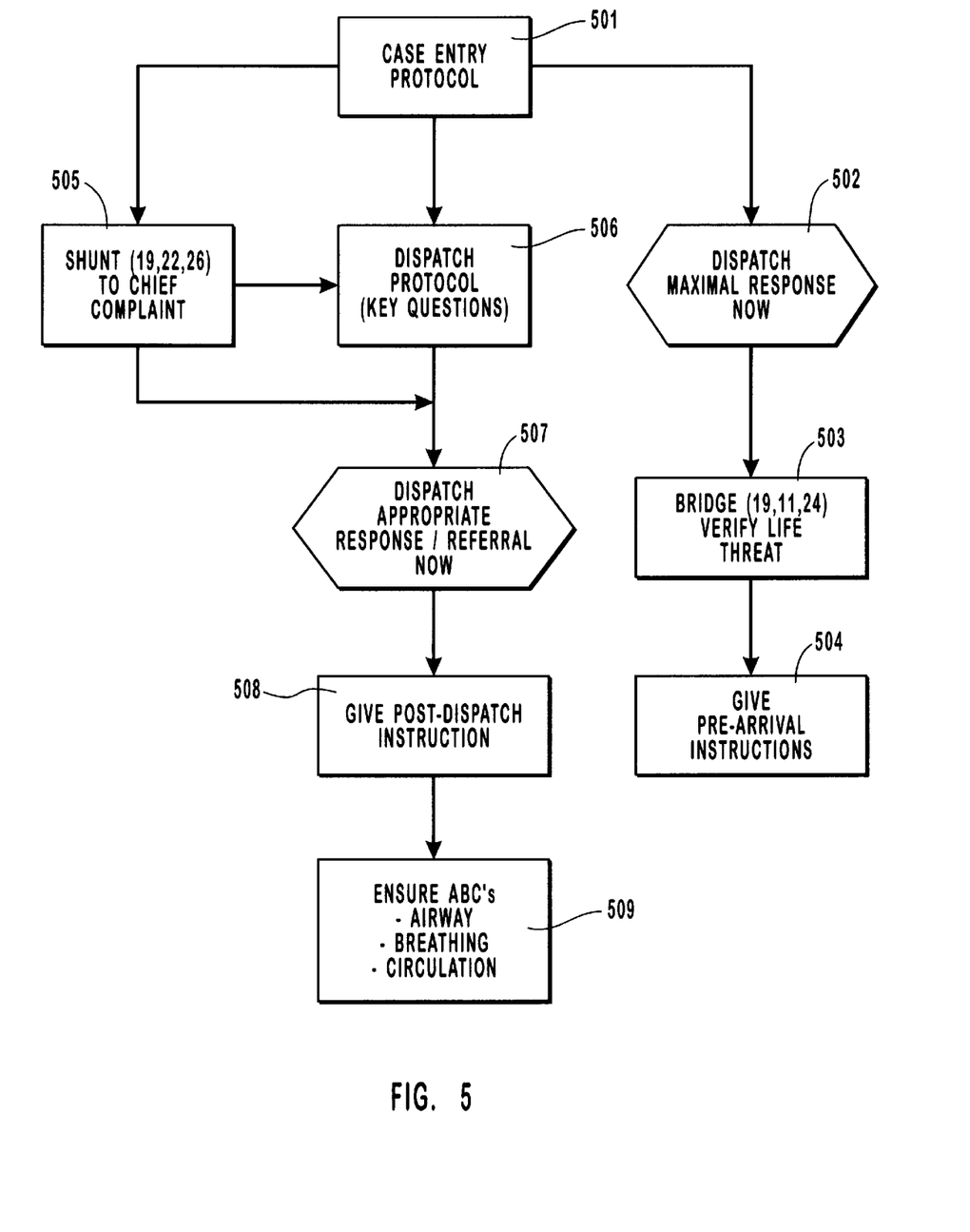
FIG. 5 depicts a top-level block diagram of the preferred systematic protocol for use by dispatchers.

FIG. 5 shows the complete system in which the invention operates in its best mode. The process of managing emergency medical dispatchers, the information they require and the information they give is detailed in FIG. 5. The case entry protocol 501, the heart of this invention, provides the initial steps through which all the emergency callers or patients are taken to provide symptom information and to access medical information. The purpose of the case entry protocol 501 is to receive sufficient information to permit the dispatcher to identify the caller's chief complaint. This critical information received during the primary interrogation 501 includes a description of the problem (or the patient's complaint), the patient's age and the status of consciousness and breathing. This information is also referred to as "the four commandments of emergency medical dispatching." If the dispatcher receives information that the patient is unconscious and not breathing (or unconscious and breathing is uncertain or conscious but not breathing where the failure to breath has been verified), for whatever reason, a maximal response 502 is sent immediately, before continuing with any further interrogation or instructions, and the caller is told to stay on the line for further instructions. The life threat is then verified 503 and pre-arrival instructions are given 504. These pre-arrival instructions 504 include six treatment sequence algorithmic scripts covering Arrest, Choking, and Childbirth. Instructions 504 are given to guide the caller through CPR, the Heimlich Maneuver, or emergency childbirth procedures. In many cases, the result of properly conveyed instructions is a more viable patient by the time field personnel arrives. Should the dispatcher learn that the patient is breathing, but the dispatcher lacks sufficient information to directly go to the Key Questions of the Dispatch Protocol 506, the dispatcher is shunted 505 to additional interrogations whose purpose is to give the dispatcher the necessary information to ascertain the caller's chief complaint while focusing on heart problems, industrial/machinery accidents and/or general sick person issues. Once the dispatcher has enough information to have identified the caller's chief complaint, the dispatcher is taken to the Dispatch Protocol 506 where additional interrogations are performed to complete "key questions." This secondary interrogation 506 typically takes approximately 30 seconds and tends to focus on the specific or chief complaint of the caller. This secondary interrogation, or Dispatch Protocol 506, provides a more orderly and closer view of the patient so that the pre-hospital care provided is appropriate and in keeping with the severity of the injury or illness. During this step 506 the dispatcher will match the symptoms, or combination of symptoms, discovered through interrogation and send the appropriate response 507. The appropriate response 507 is determined through a system of assigning determinant levels and numbers, from A2 generally less serious to D1 generally very serious. When the dispatcher identifies a determinant in one of the four levels (Alpha-A, Bravo-B, Charlie-C, and Delta-D) the response configuration (emergency vehicles and the mode of response) is dispatched as indicated by the response protocol. After the responders (field emergency medical care-givers) has been sent, the dispatcher remains on the telephone with the caller to give instructions 508 regarding what to do, and what not to do, prior to the arrival of the responders. This information is taken from the "Post-Dispatch Instructions" section of the protocols and provided whenever possible and appropriate. A main purpose of these "Post-Dispatch Instructions" 508 is to prepare the patient for and to expedite the field personnel's work at the scene. "Post-Dispatch Instructions" include such instructions as to collect the patient's medications, write down the name of the family doctor and put away pets. Each caller is also instructed to ensure 509 that the patient has an open airway, is breathing, is given nothing to eat or drink before responders arrive and, if necessary, how to treat for shock using the procedure given in the reference script for Airway, Breathing, and Circulation. Callers are routinely advised to "call back if the patient's condition worsens for further instructions."

Figure 6:
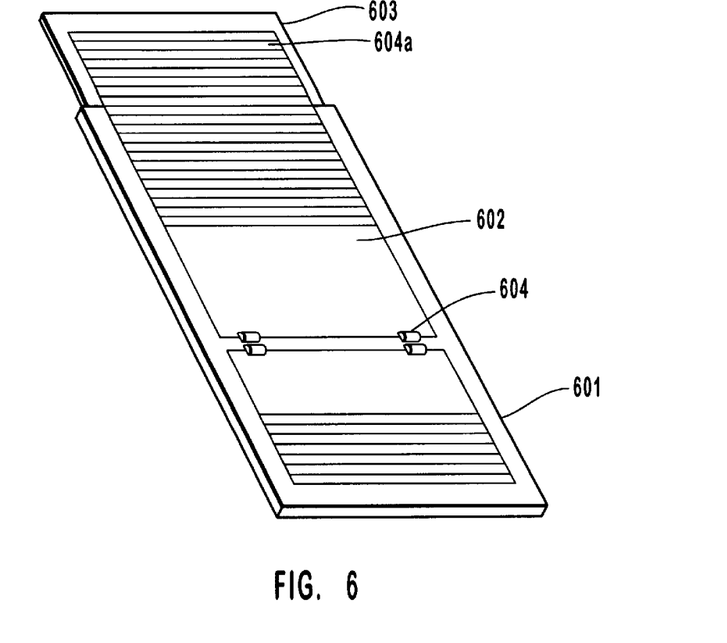
FIG. 6 depicts the flip card apparatus showing a preferred embodiment of protocol guidance system.

FIG. 6 depicts an embodiment of the flip card apparatus showing a preferred system for the use of the invention. One preferred embodiment of the invention involves the use of a flip card apparatus 601. The flip card apparatus 601 has the advantage of organizing the cards 602 so that the top or bottom, label edge of each card can be seen by the user. Each card 602 is separately fastened into the apparatus with one or more fasteners 604. The steps embodying the elements of this invention, the entry protocol, are displayed on a top flap 603 and the first card 604a. Alternative embodiments of the card apparatus can be a deck of cards bound in a manner well known to those skilled in the art. In the current embodiment of the flip card apparatus there are sixty-four chief complaint cards, twelve pre-arrival instruction cards, two post-dispatch cards, one determinant classification card and two entry protocol cards. The cards are generally organized in pairs, with the top card providing the protocol questions, instructions, jump directions and determinant assignments. The bottom card provides information the dispatcher uses to improve the dispatcher's decision making process.

Figure 7:
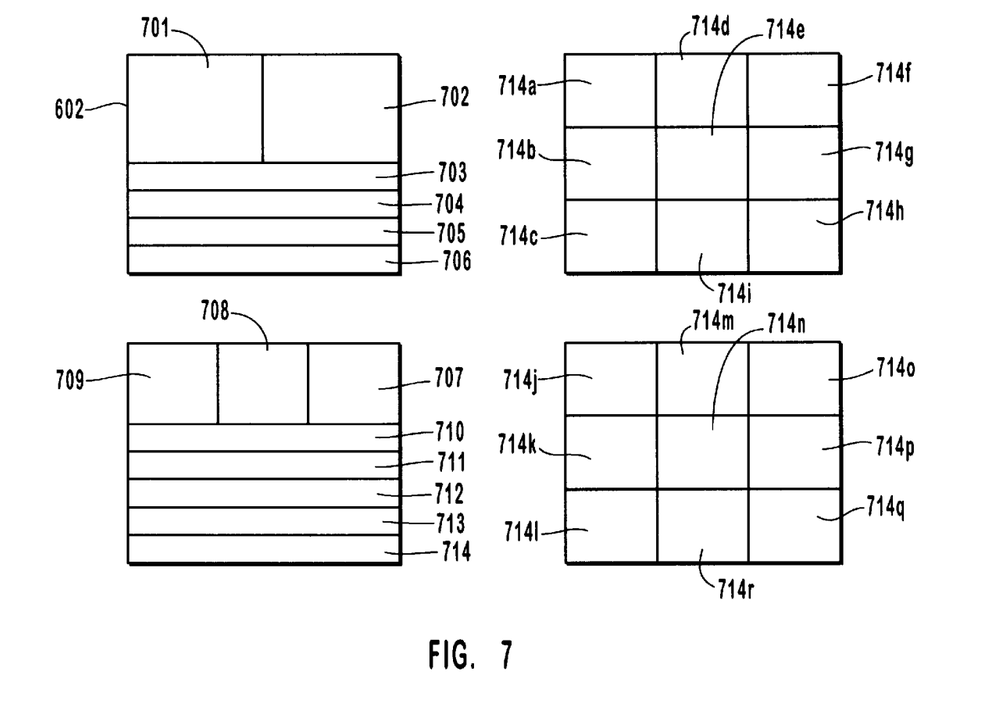
FIG. 7 depicts a view of the sections of a typical flip card used in the flip card apparatus.

FIG. 7 shows a view of the sections of a typical flip card, as used in the flip card apparatus embodiment of the invention. The typical flip card 602 is divided into logical sections for ease of use and consistency. A key question section 701 is provided as a script to the dispatchers to ensure that all key questions are asked in a calm, consistent, systematic manner. After all key questions are asked from the key question section 701, typically the dispatcher determines the appropriate determinant level. Sections A-Alpha 703, B-Bravo 704, C-Charlie 705 and D-Delta 706 are provided to aid the dispatcher in making the determinant designation. Each determinant level may have one or more sublevels. Generally, the most critical call is given a determinant level of D-Delta and the least critical call is given a determinant level of A-Alpha. The more critical the determinant level assigned to a call, the more medical resources and urgency may be applied to provide help. For example, an A-Alpha call will typically be responded to by emergency medical technicians and an ambulance proceeding to the patient under the safest method reasonably possible, while a D-Delta call will typically be responded to by the closest emergency medical technicians, an ambulance, paramedics, all who will proceed under the most urgent method possible. Sublevels may not indicate the criticality of the call, rather sublevel designations indicate the type of call, information often especially important to the dispatched medical team. After the determinant code is determined 703–706 the dispatcher is referred to the post-dispatch instructions section 702. The purpose of the post-dispatch instructions is to systematically prepare for and expedite the field personnel's job at the scene, and prevent further harm to the patient or others at the scene. The post-dispatch instruction section 702 includes such instructions as collecting the patient's medications, writing down the name of the family doctor and securing animals in the area. Each caller is also instructed, from the post-dispatch instruction section 702, to ensure that the patient has an open airway, is breathing, is given nothing to eat or drink before responders arrive, and, if needed, how to treat for shock using a reference script. Callers are also routinely advised to "call back if the patient's condition worsens for further instructions." Prearrival instructions 506 are provided on alternative cards 714, subsectioned as shown in FIG. 7 as 714a–r. These pre-arrival instruction sections 714 provide scripted treatment sequences for arrest, choking and childbirth. These procedures, provided through sections 714, guide the caller through CPR, the Heimlich Maneuver or emergency childbirth procedures. Sections 707 to 714 provide important information to the dispatcher for the dispatcher's use in providing more educated responses. This information includes such information as categorizations of dangerous areas or injuries; types of injuries; symptoms; rules and axioms. Such information as is systematically provided to place the key questions of section 701, the determinant classifications of sections 703–706, and the post-dispatch instructions of section 702 into context for the dispatcher.

Figure 8:
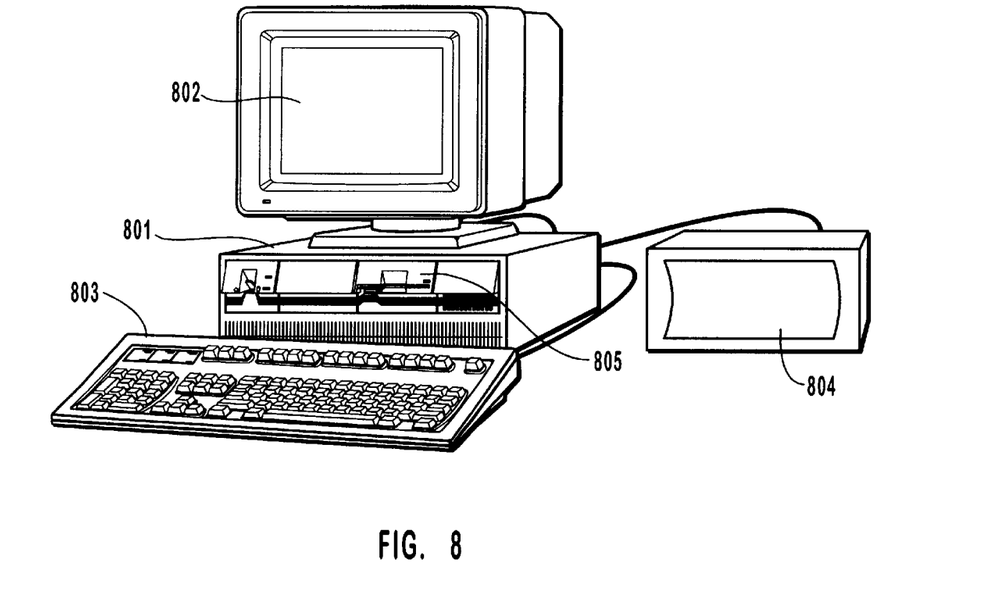
FIG. 8 shows a system diagram showing the components of a typical computer system used in the computerized embodiment of this invention.

FIG. 8 shows a system diagram of the components of a typical computer system used in the computerized embodiment of the invention. A second preferred embodiment of the invention is designed to operate in combination with a computer system using specially designed computer software incorporating the procedure of the invention. A typical computer system used in combination with software incorporating the invention includes a processing unit 801 to execute the instructions of the software; a display unit 802 to provide the means for providing the dispatcher with the prompts and information necessary to practice the invention; an input device 803 to provide the means for the dispatcher to interact with the software version of the invention; a storage device 805 for storage of the software and the files associated with the invention; and an output device 804 for printing reports and other information.

Figure 9:
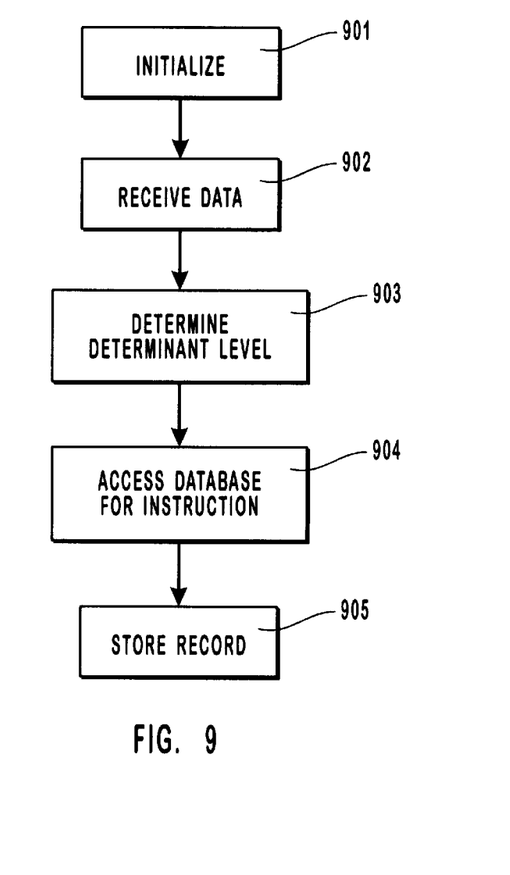
FIG. 9 depicts a flow chart representation of the preferred top level steps of the systematic protocol used with this invention.

FIG. 9 shows a process flow chart representation of the preferred top-level steps of the invention. The software embodiment of the procedure of the invention is accomplished by performance of a number of procedural steps. First, the software is initialized 901. Data is received 902 following the request for information from the caller. As data is received 902, the determinant level is determined 903. Intermediate determinant levels are produced as information is received and processed, the final determinant level is only achieved after all necessary information is received and processed. A database is accessed 904 to produce the appropriate instructions for communication with the caller. Records of the calls and queries are stored 905, for historical reports, for review of the dispatchers and for continued quality assurance control.

It is to be understood that the above-described embodiments are merely illustrative of numerous and varied other embodiments which may constitute applications of the principles of the invention. Such other embodiments may be readily devised by those skilled in the art without departing from the spirit or scope of this invention and it is our intent that they be deemed within the scope of our invention.

I claims:

1. A method for grading a medical dispatcher's performance in adhering to a provided protocol, using a computer system comprising:
   a central processing unit;
   dynamic memory,
   static memory,
   a display device,
   an input device,
   an output device,
   a mass storage device which contains
      a number of emergency medical instruction records,
      a number of medical information records,
      a grouping of determinant codes,
      a number of emergency medical inquiry reports, the method comprising the steps of:
         (A) receiving an inquiry from an emergency medical caller;
         (B) processing said received inquiry by a dispatcher;

(C) selecting said processed inquiry for review;
(D) reviewing said processed inquiry for compliance with the systematic protocol;
(E) scoring said processed inquiry to establish a method of ranking and comparing said reviewed processed inquiry;
(F) preparing reports of said scored processed inquiry; and
(G) educating the dispatcher to improve performance in the future based on said prepared reports.

* * * * *